(12) United States Patent
Keller et al.

(10) Patent No.: US 7,115,274 B2
(45) Date of Patent: Oct. 3, 2006

(54) METHOD OF USING AUTOLOGOUS FIBROBLASTS TO PROMOTE HEALING OF WOUNDS AND FISTULAS

(75) Inventors: Gregory S. Keller, Santa Barbara, CA (US); Elena Revazova, Westwood, CA (US)

(73) Assignee: Isolagen Technologies, Inc., Houston, TX (US)

( * ) Notice: Subject to any disclaimer, the term of this patent is extended or adjusted under 35 U.S.C. 154(b) by 0 days.

(21) Appl. No.: 11/040,419

(22) Filed: Jan. 21, 2005

(65) Prior Publication Data

US 2005/0147596 A1 Jul. 7, 2005

Related U.S. Application Data

(62) Division of application No. 09/980,150, filed as application No. PCT/US00/14743 on May 26, 2000, now abandoned.

(60) Provisional application No. 60/136,457, filed on May 28, 1999.

(51) Int. Cl.
*A61F 2/02* (2006.01)

(52) U.S. Cl. ...................................... 424/423

(58) Field of Classification Search ................. 424/423
See application file for complete search history.

(56) References Cited

U.S. PATENT DOCUMENTS 5,866,167 A * 2/1999 Van Bossuyt ............... 424/520

* cited by examiner

*Primary Examiner*—Carlos A. Azpuru
(74) *Attorney, Agent, or Firm*—Fish & Richardson P.C.

(57) ABSTRACT

The present invention provides a method of using autologous fibroblasts to promote wound or fistula healing in an animal.

22 Claims, No Drawings

METHOD OF USING AUTOLOGOUS FIBROBLASTS TO PROMOTE HEALING OF WOUNDS AND FISTULAS

This application is a divisional, and claims priority, of U.S. application Ser. No. 09/980,150, filed Aug. 5, 2002, now abandoned which was a 35 U.S.C. § 371 application of International Application No. PCT/US00/14743, filed May 26, 2000, which claimed priority of U.S. Provisional Application No. 60/136,457, filed May 28, 1999. The disclosures of U.S. application Ser. No. 09/980,150, International Application No. PCT/US00/14753, and U.S. Provisional Application No. 60/136,457 are incorporated herein by reference in their entirety.

TECHNICAL FIELD OF THE INVENTION

The present invention relates to a method of using autologous fibroblasts to promote healing of wounds and fistulas in an animal.

BACKGROUND OF THE INVENTION

In patients undergoing radial forearm free flap harvest, such as for the purpose of head and neck region reconstruction, approximately 23–55% of the patients experience donor site skin graft failure that results in delayed wound healing. Treatment usually requires prolonged immobilization of the forearm and hand. Such treatment adversely affects daily activities and, in the long term, can impair range of motion in the hand. In addition, some patients eventually require further surgery to reconstruct the nonhealing forearm donor site. (See, for example, Chang et al., Microsurgery 17:136–140 (1996)).

In view of the above, it would be desirable to provide a method of promoting healing of a radial forearm free flap site that does not require prolonged immobilization of the forearm and hand. It also would be desirable to provide a method of promoting healing of a radial forearm free flap site that does not require further surgery to reconstruct the nonhealing donor site. Such a method also would have utility in the treatment of other nonhealing wounds.

A fistula is an abnormal communication between two epithelialized surfaces, e.g., the skin and a hollow organ. Types of fistulas include enterocutaneous, esophageal/tracheal, bronchopleural and anal fistulas. The etiology of an enterocutaneous fistula is usually iatrogenic (75–85%), i.e., following surgery, in particular alimentary tract surgery, or instrumentation, although an enterocutaneous fistula can be due to the presence of a tumor, an infection, an inflammation, ischemia or exposure to radiation. Fistulas can be classified as "high output," if their output is greater than 500 ml over a 24 hr period, and "low output," if drainage is less than 500 ml over a 24 hr period (Foster et al., Surg. Clin. N. Am. 76(5): 1019–1033 (1996)).

The major causes of mortality due to enterocutaneous fistulas are sepsis, electrolyte disturbance and malnutrition. Enterocutaneous fistulas result in the loss of fluid, trace elements, protein and minerals (Edmunds et al., Ann. Surg. 152: 445–471 (1960)). Reported rates of enterocutaneous fistulas range from 6.5% to 21%. There also can be considerable morbidity and, in particular, fistula effluent can result in escoriation and maceration of surrounding skin (Foster et al. (1996), supra).

The spontaneous rate of fistula closure is 60–75%. Fistulas fail to close spontaneously for a number of reasons. Nonhealing of certain enterocutaneous fistulas is associated with adjacent abscess, intestinal discontinuity, distal obstruction, poor adjacent bowel, a fistula tract that is less than 2 cm in length, radiation damage, carcinoma, enteral defects greater than 1 cm and location, such as the stomach, the lateral duodenum, the ligament of Treitz and the ileum (Berry et al., Surg. Clin. N. Am. 76(5): 1009–1017 (1996); and Edmunds et al. (1960), supra).

Current approaches to promote fistula closure can be time-consuming and considerably costly to the patient and the medical community. Although management of enterocutaneous fistulas with parenteral nutrition and suppression of gastrointestinal secretions with somatostatin analogues results in decreased fistula output, an increase in the rate of fistula closure has not been observed with such treatment. Some investigative efforts have focused on identification of nutritional constituents, which could improve mucosal healing. Not uncommonly, however, the patient faces surgical exploration with excision of the fistula tract. Furthermore, in the debilitated patient, the surgical management of a chronic non-healing fistula may be dangerous, if not impossible.

There have been numerous reports of the use of various sealants, including synthetic and biological sealants, such as the use of isobutyl-2-cyanoacrylate (Histoacryl) and fibrin to close refractory enterocutaneous fistulae (Shand et al., Gastrointest. Endoscopy 46(4): 357–358 (1997); and Cellier et al., Gastrointest. Endoscopy 44(6): 731–733 (1996)). All have met with limited success. Use of the fibrin sealant, which may stimulate local fibroplasia, may, at times, be cumbersome, requiring injection in rapid succession of human fibrinogen and thrombin, which may initiate and enhance signals required for neovasularization and wound healing (Santos et al., Hepato-Gastroentero. 44: 1085–1089 (1997)), usually onto an absorbable fabric to prevent the sealant from being flushed from the fistulous tract. Results have been best when injections are performed from the internal and external opening of the tract in the case of gastrocutaneous fistulas, requiring endoscopic intervention. This technique, therefore, is limited by the reach of the endoscope, and fistulas located more distally in the alimentary tract remain a problem. For these more distally located fistulas, there has been some limited experience with injecting sealant through a catheter advanced through the tract under fluoroscopic guidance (Santos et al. (1997), supra). However, long-term occlusion is not always achieved. In addition, inherent to the use of biological agents is the possibility of transmission of infectious agents.

In view of the above, it would be highly desirable to provide a method of promoting healing of a fistula that is minimally invasive, speeds the process of fistula closure, has the potential to avoid surgery, and provides significant cost savings through reduced hospital stay and chronic requirements for parenteral nutrition.

Therefore, it is an object of the present invention to provide a method of promoting healing of a wound or fistula in an animal. This and other objects and advantages of the present invention, as well as additional inventive features, will become apparent from the description set forth herein.

BRIEF SUMMARY OF THE INVENTION

The present invention provides a method of promoting healing of a wound or a fistula in an animal, such as a mammal, in particular a human. Desirably, the wound or the fistula is susceptible to healing upon administration of autologous fibroblasts. The method comprises (a) obtaining autologous fibroblasts and (b) administering the autologous fibroblasts to a wound or a fistula in the animal, wherein the autologous fibroblasts promote healing of the wound or the fistula. Preferably, the autologous fibroblasts are obtained from a tissue which is the same type of tissue as a tissue of which the wound is comprised or a tissue in which the fistula exists, as appropriate. Also preferably, the autologous fibroblasts are cultured in the animal's own serum. The fibroblasts are preferably passaged in culture less than about ten times, more preferably from about four to about six times. About 20 million autologous fibroblasts are preferably administered per administration.

DETAILED DESCRIPTION OF THE INVENTION

The present invention is predicated on the surprising and unexpected discovery that exogenously administered autologous fibroblasts can promote healing of a wound or fistula. In view of this discovery, the present invention provides, in one embodiment, a method of promoting wound healing in an animal, such as a mammal, in particular a human. The present inventive method of promoting healing of a wound, such as a radial forearm free flap site, is advantageous inasmuch as it is speeds wound healing and, in the context of a radial forearm free flap site, obviates prolonged immobilization of the forearm and hand and reconstructive surgery of the nonhealing site.

In another embodiment, the present invention provides a method of promoting fistula healing in an animal, such as a mammal, in particular a human. The present inventive method of promoting healing of a fistula is advantageous inasmuch as it is minimally invasive and speeds fistula closure, thereby avoiding surgery and providing significant cost savings through reduced hospital stay and chronic requirements for parenteral nutrition.

Desirably, the wound or fistula is one that is susceptible to healing upon administration of autologous fibroblasts. For example, it will be appreciated by one of ordinary skill in the art that some wounds, given the nature, extent or age of the wounds or the presence of complications, simply can not be healed. Desirably, the wound is one that has just occurred or has just been discovered and is of such a size and nature that it is susceptible to healing in accordance with the method of the present invention.

The method comprises (a) obtaining autologous fibroblasts and (b) administering the autologous fibroblasts to a wound or a fistula in an animal, such as a mammal, in particular a human, wherein the autologous fibroblasts promote healing of the wound or the fistula. In the context of the method of the present invention, the fibroblasts are believed to promote wound and fistula healing by producing extracellular matrix that contains many cytokines, including fibroblast growth factor, which stimulates angiogenesis and cell migration. In addition, fibroblasts undergo phenotypic transformation into myofibroblasts, which play a critical role in wound and fistula contraction (i.e., closure). The use of autologous fibroblasts, such as those derived from the dermis, fascia, connective tissue, or lamina propria, mitigates against the possibility of an immunogenic reaction due to a lack of tissue histocompatibility.

Autologous fibroblasts are obtained from an animal, such as a mammal, in particular a human, in accordance with methods known in the art (see WO 98/36704). Preferably, the autologous fibroblasts are obtained by isolating fibroblasts from the same type of tissue as a tissue of which the wound is comprised or a tissue in which the fistula exists, as appropriate. Techniques used to isolate fibroblasts from a given tissue are known in the art.

Given that fibroblasts generally cannot be isolated in sufficient numbers for use in the present invention, preferably the fibroblasts are cultured. Methods of culturing fibroblasts, including culture media and culturing techniques, such as passaging and selection (see WO 98/36704) are also known in the art. A preferred method of culturing fibroblasts from a skin biopsy or an oral mucosa biopsy is set forth in Example 1. While the fibroblasts can be cultured in any suitable culture medium, such as culture medium comprising bovine serum albumin or fetal calf serum, preferably the fibroblasts are cultured in serum-free medium or medium comprising the animal's own serum, thereby reducing the possibility of the animal undergoing an immunogenic reaction to the fibroblasts upon administration. Immunogenic reaction also can be reduced by late-stage passage of the cultured autologous fibroblasts and repeated washing in a physiologically compatible buffer, such as phosphate-buffered saline, after which the washed fibroblasts can be cultured in serum-free medium containing the requisite growth factors as are known in the art for a period of 2–24 hours (see WO 98/36704).

The cultured fibroblasts should be passaged at regular intervals. The fibroblasts should be passaged a sufficient number of times to ensure a substantially pure population of fibroblasts but not so many times that the fibroblasts undergo undesirable changes in culture. Preferably, the fibroblasts are passaged in culture less than about ten times, more preferably from about four to about six times. Adjustments to the culture medium and time and frequency of passages can and should be made as required in view of the patient and tissue sources of the fibroblasts.

Preferably, collagen-producing fibroblasts are selected. Selection techniques (e.g., flow cytometry and magnetic bead selection) that can be used to select for collagen-producing fibroblasts are known in the art and exemplified herein.

Preferably, fibroblasts are removed from early cultures for freezing and long-term storage on an as-needed basis during the early passage stages of culture. Freezing of fibroblasts and their use to inoculate secondary cultures is also known in the art (see WO 98/36704). Preferably, when a vial of frozen cells is removed from the freezer, the vial is immediately transferred to a water bath at 37° C. As soon as the sample has thawed, the exterior surface of the vial is sterilized with, for example, ethanol. Then, the cells are diluted, preferably with 7 mls of serum-containing medium, and added to flasks (25 cm², for example) for secondary culture.

After the fibroblasts in culture have reached confluence, the fibroblasts can be processed for administration, such as by injection, or further cultured to form a three-dimensional "tissue" for subsequent surgical engraftment. Fibroblasts can be suspended in a collagen gel matrix for purposes of injection (see WO 98/36704). Alternatively, three-dimensional "tissue" can be formed as described in WO 98/36704.

A preferred embodiment of the present invention is the use of autologous fibroblasts to promote healing of a wound, in particular a chronic non-healing wound. In particular, wounds of the epithelium, such as those due to venous stasis or radiation, can be treated with the method of the present invention. In addition, wounds of the mucosa, such as those due to gastric/duodenal ulcer or anal fissure, can be treated with the method of the present invention.

Another preferred embodiment of the present invention is the use of autologous fibroblasts to promote healing of a fistula, such as an iatrogenic fistula (i.e., fistula following surgery or instrumentation) or a spontaneous fistula (e.g., due to infection, inflammation, ischemia, carcinoma or radiation). The present inventive method can be used to promote healing of an enterocutaneous fistula, such as a gastric, duodenal, pancreatic, jejunal, ileal or colonic fistula. The method also can be used to promote healing of an esophageal/tracheal fistula, such as a tracheoesophageal, tracheocutaneous or esophagocutaneous fistula. Healing of a bronchopleural fistula or an anal fistula (i.e., fistula-in-ano) also can be promoted with the present inventive method. The present inventive method also is believed to be useful in the treatment of acute wounds, including puncture wounds, wounds associated with autoimmune disease, bed sores, wounds associated with chemical ingestion or inhalation, such as those associated with cocaine abuse, and other wounds of the sinus, lung and vagina.

The autologous fibroblasts are administered to a wound or fistula in an animal, such as a mammal, in particular a human, in accordance with methods known in the art. Any suitable route of administration can be used provided that the chosen route effects delivery of the autologous fibroblasts to the site of the wound or fistula. Autologous fibroblasts can be administered to promote healing of a wound of the skin using methods set forth in WO 98/36704. Administration of autologous fibroblasts in the promotion of healing of a gastric/duodenal ulcer is preferably by endoscopic injection. Administration of autologous fibroblasts in the promotion of healing of a fistula is preferably by injection of the external fistula tract opening as well as internal endoscopic injection. Preferably, the fibroblasts are administered in a biologically, e.g., pharmaceutically acceptable form. Such formulations are known in the art (see, e.g., *Remington's Pharmaceutical Sciences*, 16$^{th}$ edition, Mack, editor (1980)).

Autologous fibroblasts should be administered to the wound or fistula as soon as possible after the wound or fistula occurs or is discovered. In this regard, the underlying cause(s) of the wound or fistula should no longer exist or should be greatly diminished or undergoing aggressive treatment—otherwise, fibroblast administration to the wound or fistula will not result in as successful healing as possible.

Preferably, about 20 million autologous fibroblasts are administered per administration. Only viable fibroblasts should be administered. In this regard, fibroblasts generally remain viable for only about 24 hours outside of culture when stored on ice. The number of autologous fibroblasts administered in any given administration may need to be adjusted up or down depending upon the potency of the fibroblasts (e.g., collagen production), which may differ with the patient and tissue sources of the fibroblasts and which can be determined in accordance with the assays set forth in Examples 2 and 3 or other assays as are known in the art.

Administrations are repeated as necessary until the wound or fistula is healed. When a repeat administration is warranted can be determined by periodic assessment by a physician, such as in the case of an ulcer or a wound, or, in the case of an intestinal fistula, by measuring fluid output. As long as there is fluid output from an intestinal fistula, fibroblasts should be periodically administered, preferably at least about once per week. Repeat administration of fibroblasts is no longer warranted for treatment of an intestinal fistula when there no longer is fluid output from the intestinal fistula, provided, however, that fluid from the intestinal fluid is not draining elsewhere in the body.

The fibroblasts can be administered with other active agents as desired. For example, the fibroblasts can be administered in conjunction with basic fibroblast growth factor, which stimulates angiogenesis and is mitogenic for growth of keratinocytes and fibroblasts in vivo.

If desired, fetal or juvenile sources of fibroblasts can be used in the context of the present invention. Since fetal cells lack immunogenic determinants, they do not elicit a rejection response to the graft.

EXAMPLES

The following examples serve to illustrate the present invention and are not intended to limit its scope in any way.

Example 1

This example describes preparation of a culture of fibroblasts obtained from a skin biopsy or an oral mucosa biopsy.

Skin and oral mucosa biopsies were dropped into sterile capped tubes containing 10 mls of tissue culture medium (Eagle's modified minimal essential (MEM) medium containing 100 μg/ml penicillin, 100 mg/ml streptomycin, 0.1 g/l sodium private and 5% patient's serum). Biopsies were kept at room temperature and "planted" immediately.

Biopsies were planted by pouring the biopsies in the culture medium from the tubes into sterile Petri dishes under a laminar flow hood. The biopsies were dissected into small pieces and distributed into 5–6 dry 60 mm tissue culture dishes with sterile silicone grease. A round 25 mm sterile coverslip was placed over a given piece of biopsy and silicone grease and pressed down. Eagle's MEM medium (0.2 ml) was added at the margin of each coverslip and was allowed to move underneath the coverslip by capillary action to displace the air beneath the cover slip. Once the coverslips had medium beneath them and no air bubbles, 5 ml of medium were added to the dishes. The dishes were placed in trays and incubated in a humidified $CO_2$ incubator with 5% $CO_2$ in air and not touched for 10 days. The cells were incubated, examined under a light microscope and, if adequate cell migration is observed at the margins, collected and concentrated in accordance with methods known in the art.

Example 2

This example describes the analysis of fibroblast potency in collagen gels by morphological observation.

Collagen gels containing fibroblasts were stained with rhodamine-labeled phalloidin, which stains actin filaments on the inner surface of the cell membranes of fibroblasts, thereby enabling observation of the morphology of fibroblasts. After the collagen gels were stained, the gels were rinsed 3 times with phosphate-buffered saline without $Ca^{2+}$ and $Mg^{2+}$ (referred to herein as PBS-neg), fixed with 4% paraformaldehyde containing 5% sucrose at room temperature for 30 min. Gels were then cut into small pieces, washed with PBS-neg 3 times every 5 min and treated with 0.2% Triton X-100 at room temperature for 5 min. The gel pieces were stained with rhodamine-labeled phalloidin for 30 min. Cells were washed with PBS-neg 3 times every 5 min and embedded with 80% glycerol. Morphological change of the fibroblasts in collagen gels were observed under an immunofluorescence microscope at 6, 12 and 18 hrs after incubation and the number of fibroblasts and the number of long cells were counted and the percentage of long cells was determined. The percentage of long cells from biopsy specimens from patients desirably should be comparable to that of controls, e.g., mucosa or skin fibroblasts from the same patient.

Example 3

This example describes the analysis of fibroblast potency in collagen gels by contraction assay.

Pepsin-processed type atelocollagen solution (0.2%; pH=7.3) was prepared by mixing 0.3% pepsin-processed type I atelocollagen solution, 6× concentrated MEM and 10% FBS according to the ratio of 4:1:1. Fibroblasts were dispersed with 0.05% trypsin and 0.02% EDTA in PBS, in which the cell density was adjusted to $1\times10^5$/ml, then suspended with 0.2% collagen gel solution and dispensed (3 ml/dish) into 35 mm plastic dishes. The dishes were then incubated at 37° C. with 5% $CO_2$ and 95% air. The collagen gels contracted in a time-dependent manner. The diameters of collagen gels were measured every 2 hrs for the first 24 hrs of incubation. Thereafter, the diameters of the collagen gels were measured every day until the $10^{th}$ day. The first medium change was performed a day after the initial incubation and then the medium was changed every other day. The diameter of collagen gel contraction with fibroblasts from patients desirably should be comparable to that of control fibroblasts, e.g., fibroblasts from the. patient's skin or mucosa.

Example 4

This example describes the use of the present inventive method to promote healing of an intestinal fistula.

A 40 year old woman, who underwent an exploratory laparotomy with a right hemicolectomy, developed an enterocutaneous fistula that persisted despite conventional treatment consisting of bowel rest and total pancteral nutrition. Although the outflow from the fistula tract decreased, she continued to have an ouput from the fistula tract of around 200–300 cc per day. The output required her to wear a collection bag.

The external opening of the fistula tract was injected twice with approximately 1 cc (each injection) of autologous fibroblasts. The output from the fistula tract decreased dramatically within a few days following the first injection. Following the second injection, the patient ceased to have any output from the fistula tract. The woman experienced minimal reaction and discomfort from the injections. Six weeks following the second injection, the woman underwent a barium enema, which confirmed that the tract had closed.

Example 5

This example describes the use of the present inventive method to promote healing of a radial forearm free flap site.

The excess tissues that are excised from the radial forearm free flap and normally discarded during flap contouring and insetting are retained. Dermal and fascial fibroblasts are harvested from the retained tissues and propagated in tissue culture. Patients who experience skin graft loss and delayed wound healing at the forearm donor site undergo local administration of autologous cultured fibroblasts in order to promote wound healing, i.e., re-epithelialization.

The documents (e.g., patents, patent applications and journal articles) cited herein are hereby incorporated in their entireties by reference.

While the present invention has been described with an emphasis upon preferred embodiments, it will be appreciated by those of ordinary skill in the art that the present invention can be practiced other than as specifically described herein. Therefore, the present invention includes those modifications encompassed within the spirit and scope of the following claims.

What is claimed is:

1. A method of promoting healing of a fistula in an animal, wherein said fistula has a fistula tract opening and is susceptible to healing upon administration of autologous fibroblasts, which method comprises:
    (a) obtaining autologous fibroblasts, and
    (b) administering the autologous fibroblasts in the form of an injection into the fistula tract opening, wherein the said autologous fibroblasts promote healing of the fistula.

2. The method of claim 1, wherein said animal is a human.

3. The method of claim 1, wherein said autologous fibroblasts are derived from a tissue which is the same type of tissue as a tissue in which the fistula exists.

4. The method of claim 1, wherein said fibroblasts are cultured in the animal's own serum.

5. The method of claim 1, wherein said fibroblasts are passaged in culture less than about ten times.

6. The method of claim 5, wherein said fibroblasts are passaged in culture from about four to about six times.

7. The method of claim 1, wherein about 20 million autologous fibroblasts are administered per administration.

8. The method of claim 1, wherein said fistula is an iatrogenic fistula.

9. The method of claim 1, wherein said fistula is a spontaneous fistula.

10. The method of claim 9, wherein said fistula is due to infection.

11. The method of claim 9, wherein the said fistula is due to inflammation.

12. The method of claim 9, wherein said fistula is due to ischaemia.

13. The method of claim 9, wherein said fistula is due to carcinoma.

14. The method of claim 9, wherein said fistula is due to radiation.

15. The method of claim 9, wherein said fistula is an enterocutaneous fistula.

16. The method of claim 15, wherein said fistula is a gastric, duodenal, pancreatic, jejunal, ileal, or colonic fistula.

17. The method of claim 1, wherein said fistula is a tracheo-esophageal fistula.

18. The method of claim 1, wherein said fistula is a tracheocutaneous fistula.

19. The method of claim 1, wherein said fistula is an esophagocutaneous fistula.

20. The method of claim 1, wherein said fistula is a bronchopleural fistula.

21. The method of claim 1, wherein said fistula is an anal fistula.

22. The method of claim 1, wherein said autologous fibroblasts are administered by injection of the external fistula tract opening and internal endoscopic injection.

* * * * *